US00PP20575P2

(12) United States Plant Patent
Wood

(10) Patent No.: US PP20,575 P2
(45) Date of Patent: Dec. 15, 2009

(54) LILAC PLANT NAMED 'PENDA'

(50) Latin Name: *Syringa hybrida*
Varietal Denomination: Penda

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/287,022

(22) Filed: Oct. 1, 2008

(51) Int. Cl.
*A01H 5/00* (2006.01)

(52) U.S. Cl. ..... Plt./248

(58) Field of Classification Search ..... Plt./248

See application file for complete search history.

*Primary Examiner*—Susan B McCormick Ewoldt
(74) *Attorney, Agent, or Firm*—C. A. Whealy

(57) ABSTRACT

A new and distinct cultivar of Lilac plant named 'Penda', characterized by its relatively compact, upright and somewhat outwardly spreading plant habit; vigorous growth habit; freely branching habit; resistance to root rot pathogens; large inflorescences with purple-colored flowers; reblooming habit; and good garden performance.

2 Drawing Sheets

Botanical designation: *Syringa hybrida.*
Cultivar denomination: 'Penda'.

BACKGROUND OF THE INVENTION

The present invention relates to a new and distinct cultivar of Lilac, botanically known as *Syringa hybrida* and hereinafter referred to by the name 'Penda'.

The new Lilac plant originated from an open-pollination during the spring of 2004 of *Syringa hybrida* 'Josee', not patented, as the female, or seed, parent with an unknown selection of *Syringa hybrida*, as the male, or pollen, parent. The new Lilac plant was discovered and selected by the Inventor during the spring of 2006 as a flowering plant within the progeny of the stated open-pollination in a controlled environment in Grand Haven, Mich.

Asexual reproduction of the new Lilac plant by softwood cuttings in a controlled greenhouse environment in Grand Haven, Mich. since the spring of 2007 has shown that the unique features of this new Lilac plant are stable and reproduced true to type in successive generations of asexual reproduction.

SUMMARY OF THE INVENTION

Plants of the new Lilac have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Penda'. These characteristics in combination distinguish 'Penda' as a new and distinct cultivar of Lilac:

1. Relatively compact, upright and somewhat outwardly spreading plant habit.
2. Vigorous growth habit.
3. Freely branching habit.
4. Resistant to root rot pathogens.
5. Large inflorescences with purple-colored flowers.

6. Reblooming habit.
7. Good garden performance.

Plants of the new Lilac can be compared to plants of the female parent, 'Josee'. Plants of the new Lilac differ from plants of 'Josee' primarily in flower color as plants of the new Lilac have purple-colored flowers whereas plants of 'Josee' have pinkish lavender-colored flowers. In addition, plants of the new Lilac are more resistant to root rot pathogens than plants of 'Josee'.

Plants of the new Lilac can be compared to plants of the *Syringa meyeri* 'Palabin', not patented. In side-by-side comparisons conducted in Grand Haven, Mich., plants of the new Lilac differed from plants of 'Palabin' primarily in flower color as flowers of plants of 'Palabin' were pale pink in color.

BRIEF DESCRIPTION OF THE PHOTOGRAPHS

The accompanying colored photographs illustrate the overall appearance of the new Lilac, showing the colors as true as it is reasonably possible to obtain in colored reproductions of this type. Colors in the photographs may differ slightly from the color values cited in the detailed botanical description which accurately describe the colors of the new Lilac.

The photograph on the first sheet is a side perspective view of a typical plant of 'Penda' grown in an outdoor nursery.

The photograph on the second sheet is a close-up view of typical inflorescences of 'Penda'.

DETAILED BOTANICAL DESCRIPTION

The aforementioned photographs and following observations, measurements and values describe plants grown in Grand Haven, Mich. during the spring and summer in an outdoor nursery and under conditions which closely approximate commercial production. Plants were four years old when the photographs and the description were taken. In the description, color references are made to The Royal Horticultural Society Colour Chart, 1995 Edition, except where general terms of ordinary dictionary significance are used.

Botanical classification: *Syringa hybrida* 'Penda'.

Parentage:

*Female, or seed, parent.*—*Syringa hybrida* 'Josee', not patented.

*Male, or pollen, parent.*—Unknown selection of *Syringa hybrida*, not patented.

Propagation:

*Type.*—By softwood cuttings.

*Time to initiate roots.*—About 18 days at 27° C.

*Time to produce a rooted young plant.*—About three months at 27° C.

*Root description.*—Fine, fibrous.

*Rooting habit.*—Freely branching; dense.

Plant description:

*Plant form and growth habit.*—Perennial shrub. Relatively compact, upright and somewhat outwardly spreading plant habit; vigorous growth habit.

*Branching habit.*—Freely branching, usually lateral branches potentially developing at every node after pinching (removal of terminal apices).

*Plant height.*—About 1 meter.

*Plant diameter* (*area of spread*).—About 1.5 meters.

Lateral branch description:

*Length.*—About 20 cm.

*Diameter.*—About 2.5 mm.

*Internode length.*—About 2.2 cm.

*Texture.*—Pubescent.

*Color, immature.*—Close to 197A.

*Color, mature.*—Close to 197C.

Foliage description:

*Arrangement.*—Opposite, simple.

*Length.*—About 2.8 cm.

*Width.*—About 2 cm.

*Shape.*—Ovate.

*Apex.*—Acute.

*Base.*—Obtuse.

*Margin.*—Entire; slightly undulated.

*Texture, upper and lower surfaces.*—Slightly pubescent.

*Venation pattern.*—Pinnate.

*Color.*—Developing and fully expanded leaves, upper surface: Close to 137A; venation, close to 137A. Developing and fully expanded leaves, lower surface: Close to 138B; venation, close to 137A.

*Petiole.*—Length: About 6 mm. Diameter: About 1 mm. Texture, upper and lower surfaces: Smooth, glabrous. Color, upper and lower surfaces: Close to 138A.

Flower description:

*Flower appearance/arrangement.*—Single salverform flowers arranged in terminal panicles. Freely flowering habit with usually about 265 flowers per inflorescence. Flowers face upright to outwardly.

*Flower longevity.*—Flowers last for about two to three weeks on the plant; flowers not persistent.

*Natural flowering season.*—Typically in mid-May and reblooming in mid-July in Grand Haven, Mich.

*Fragrance.*—Moderate; sweet, pleasant.

*Inflorescence height.*—About 10 cm.

*Inflorescence diameter.*—About 7 cm.

*Flower diameter.*—About 8 mm.

*Flower length* (*height*).—About 1.4 cm.

Flower bud.—Length: About 5 mm. Diameter: About 2 mm. Shape: Funnelform. Color: Close to 83A.

*Petals.*—Arrangement/quantity: Single whorl of four to six petals; petals fused towards the base to form a tube. Length: About 2.5 mm. Width: About 1.5 mm. Shape: Ovate. Apex: Acute. Margin: Entire. Texture, upper and lower surfaces: Smooth, glabrous. Color: When opening and fully opened, upper surface: Close to 77B; color becoming closer to 77A with development. When opening and fully opened, lower surface: Close to 77A.

*Sepals.*—Extremely minute (less than 1 mm by 1 mm in size) and inconspicuous.

*Peduncles.*—Length: About 9 cm. Diameter: About 5 mm. Strength: Strong, flexible. Texture: Smooth, glabrous. Color: Close to 197A.

*Pedicels.*—Length: About 2 mm. Diameter: About 1 mm. Strength: Strong, flexible. Texture: Smooth, glabrous. Color: Close to 77A.

*Reproductive organs.*—Androecium: Anther shape: Oblong. Anther size: About 2 mm by 1 mm. Anther color: Close to 77A. Amount of pollen: Scarce. Pollen color: Close to 201B. Gynoecium: Pistil length: About 3 mm. Style length: About 2 mm. Style color: Close to 77B. Stigma appearance: Rounded. Stigma color: Close to 155A.

*Seeds/fruits.*—Seed and fruit development have not been observed on plants of the new Lilac plant.

Garden performance: Plants of the new Lilac have been observed to have good garden performance and to tolerate rain, wind and temperatures ranging from about −31C to about 38° C.

Pathogen/pest resistance: Plants of the new Lilac have been observed to be resistant to root rot pathogens that are common to Lilacs. Plants of the new Lilac have not been shown to be resistant to pests and other pathogens common to Lilac.

It is claimed:

1. A new and distinct Lilac plant named 'Penda' as illustrated and described.

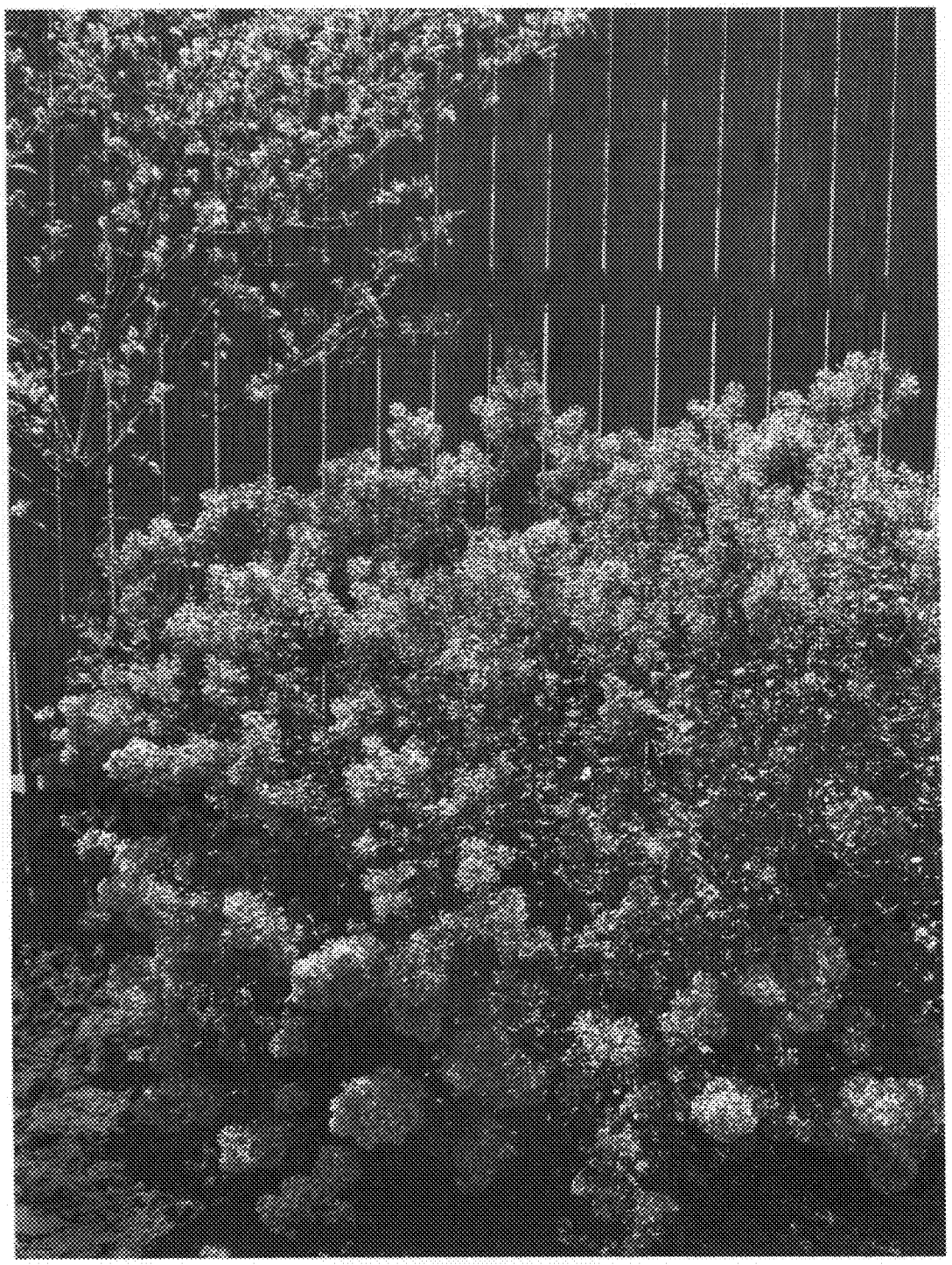

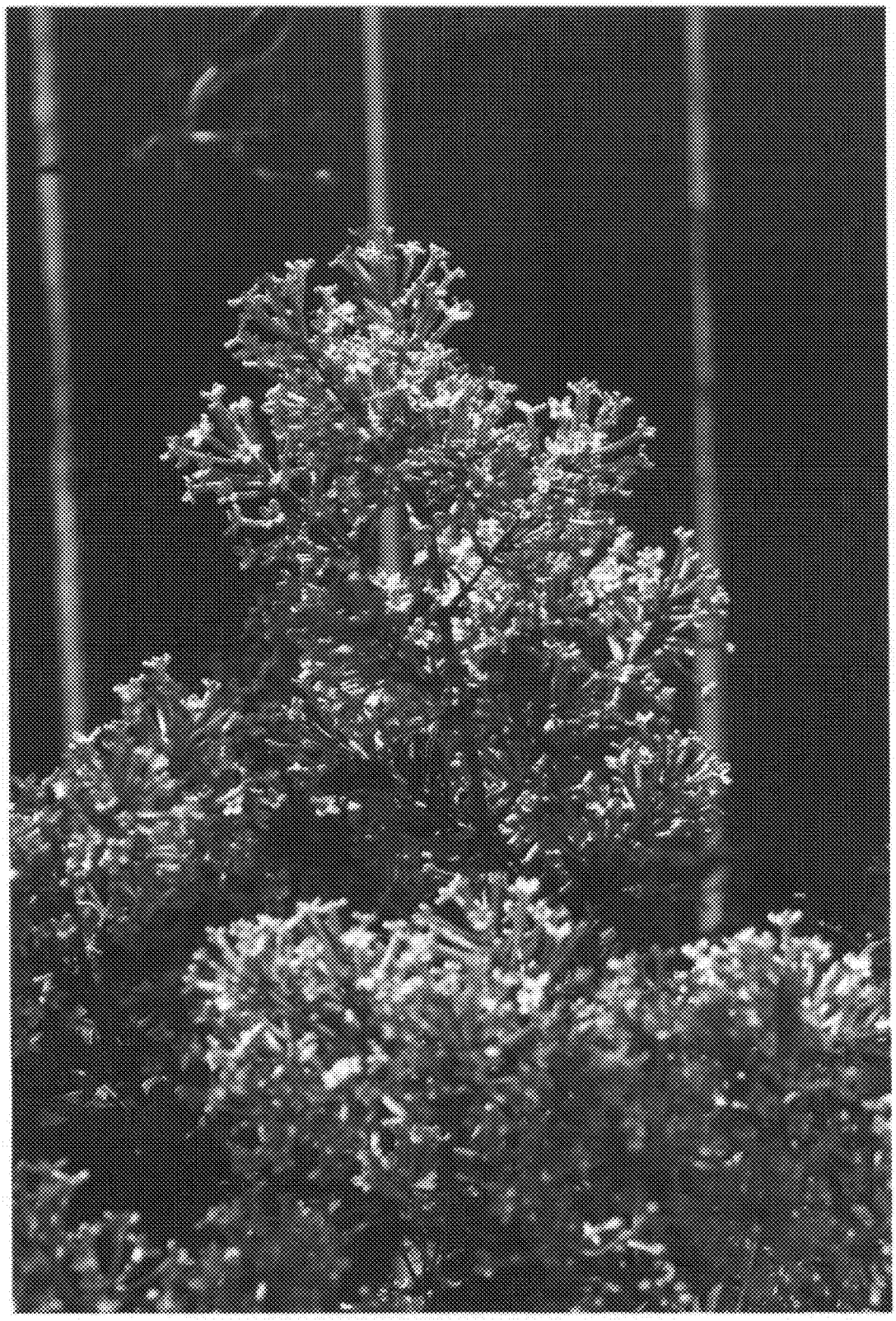

* * * * *